United States Patent [19]

Sjogren

[11] Patent Number: 4,670,039
[45] Date of Patent: Jun. 2, 1987

[54] TIMED RELEASE FERTILIZER COMPOSITION AND MEANS

[75] Inventor: Robert D. Sjogren, St. Paul, Minn.

[73] Assignee: Metropolitan Mosquito Control District, St. Paul, Minn.

[21] Appl. No.: 838,423

[22] Filed: Mar. 7, 1986

Related U.S. Application Data

[63] Continuation of Ser. No. 712,325, Mar. 14, 1985, abandoned, which is a continuation of Ser. No. 472,737, Mar. 7, 1983, abandoned.

[51] Int. Cl.$^4$ .......... C05B 11/04; C05B 7/00; A01N 25/00; C04B 11/00
[52] U.S. Cl. .......... 71/34; 71/51; 71/64.11; 71/64.13; 71/903; 106/110
[58] Field of Search .......... 71/34, 47, 51, 64.01, 71/64.11, 64.13, 903; 106/110

[56] References Cited

U.S. PATENT DOCUMENTS

| Re. 27,238 | 11/1971 | Stansbury et al. | 71/64.11 X |
|---|---|---|---|
| 2,404,698 | 7/1946 | Dreyling | 167/30 |
| 2,877,599 | 3/1959 | Hebestreet et al. | 71/903 X |
| 3,125,411 | 3/1964 | Bridger et al. | 71/64.11 X |
| 3,264,184 | 8/1966 | Geiger | 167/53 |
| 3,279,995 | 10/1966 | Reid | 71/64.11 X |
| 3,576,760 | 4/1971 | Gould et al. | 252/403 |
| 3,882,226 | 5/1975 | Brandburne | 424/19 |
| 3,891,759 | 6/1975 | Aries | 424/219 |
| 3,950,181 | 4/1976 | Pilgrim | 106/306 |
| 3,953,378 | 4/1976 | Lasser | 252/522 |
| 4,019,889 | 4/1977 | Kealy | 71/64.11 X |
| 4,023,955 | 5/1977 | Mueller | 71/64.11 |
| 4,056,610 | 11/1977 | Barber, Jr. et al. | 424/32 |
| 4,082,533 | 4/1978 | Wittenbrook et al. | 71/64.11 X |
| 4,163,674 | 8/1979 | Been | 106/15.05 |
| 4,225,693 | 9/1980 | McCormick | 526/261 |
| 4,272,398 | 6/1981 | Jaffe | 252/316 |
| 4,540,439 | 9/1985 | Kurandt | 106/110 X |

FOREIGN PATENT DOCUMENTS

| 1047272 | 1/1979 | Canada | 71/64.11 |
|---|---|---|---|
| 2021259 | 11/1971 | Fed. Rep. of Germany | 71/64.11 |
| 2655450 | 6/1977 | Fed. Rep. of Germany | 71/64.11 |
| 2743485 | 3/1979 | Fed. Rep. of Germany | 71/64.11 |
| 0075569 | 6/1977 | Japan | 71/64.11 |

OTHER PUBLICATIONS

"What Gypsum Plasters Can Do For You", United States Gypsum Company, ©1977.
"Plaster Mixing Procedures", Bulletin No. TAC150 of U.S. Gypsum Company.
"Drying of Plaster Casts", Bulletin No. TAC 148.

Primary Examiner—Donald R. Valentine
Attorney, Agent, or Firm—Merchant, Gould, Smith, Edell, Welter & Schmidt

[57] ABSTRACT

A controlled slow release fertilizer composition comprising an encapsulated fertilizer, carbon and plaster.

23 Claims, No Drawings

TIMED RELEASE FERTILIZER COMPOSITION AND MEANS

This is a continuation of application Ser. No. 06/712,325, filed Mar. 14, 1985, now abandoned, which is a continuation of application Ser. No. 472,737, filed Mar. 7, 1983, now abandoned.

FIELD OF THE INVENTION

The invention relates to a fertilizer composition and a fertilizer means which can be distributed throughout the environment to slowly release an effective growth promoting amount of fertilizer throughout the temperate months.

BACKGROUND OF THE INVENTION

Fertilizers are materials added to soils to supply elements required for plant nutrition. They may be products manufactured for the purpose, by-products of the manufacture of other chemicals, or natural materials. Fertilizer consumption has increased rapidly in the last quarter century and fertilizers manufactured for agricultural purposes have become a major product of the chemical industry world-wide.

Plants require several materials for adequate nutrition. The principal ones, carbon dioxide and water, are usually available in adequate amounts from the atmosphere and soil, and are continually replenished by natural means. Other essential nutrients are normally available in the soil but are not replenished by nature after plant utilization. Agricultural areas can as a result of intensive cultivation be substantially depleted of important nutrients. In addition to carbon, hydrogen and oxygen, 13 nutrients have been identified as essential to plant nutrition, including nitrogen, phosphorous, potassium, calcium, magnesium, sulphur, iron, manganese, copper, zinc, boron, molybdenum and chlorine. Of these elements, nitrogen, phosphorous and potassium are needed by plants in relatively large quantities and are called major elements or macronutrients. Calcium, magmesium and sulphur are normally required in lesser amounts and are considered secondary nutrients, while the remaining elements are known as micronutrients or trace elements because their requirements are very small.

The fertilizer elements discussed above are most commonly applied to the soil in the form of ammonia ($NH_3$), ammonium nitrate ($NH_4NO_3$), ammonium sulfate ($[NH_4]_2SO_4$), urea ($[NH_2]_2CO$), sodium nitrate ($NaNO_3$), calcium nitrate ($Ca(NO_3)_2$), ammonium chloride ($NH_4Cl$), monocalcium phosphate ($CaH_2[PO_4]\cdot H_2O$), dicalcium phosphate ($Ca_2HPO_4$), potassium chloride ($KCl$), potassium sulfate ($K_2SO_4$), monoammonium phosphate ($NH_4H_2PO_4$, diammonium phosphate ($NH_4)_2HPO_4$, and others.

Fertilizers have been encapsulated using resinous encapsulating agents in order to provide slow release of the fertilizer compositions into the environment. However, many of the encapsulation processes produce a product which is prohibitively expensive for agricultural purposes. Most agricultural fertilizers are commodity chemicals which are very low in cost.

One problem that exists with most common fertilizers is that they tend to release nitrogen and other fertilizing components rapidly into the soil. The rapid release of the fertilizing components can tend to harm plant roots and stems and can often result in growth of plant parts which are not desirable, such as stems and leaves, at the expense of reduced yield.

Further, many fertilizer compositions such as ammonium nitrate can be explosive in concentrated form. Accordingly, a substantial need exists to provide an encapsulated slow release fertilizer composition means which can release fertilizer elements at a rate such that the plant is not harmed and the fertilizer is utilized by the plant for improving crop yield.

BRIEF DISCUSSION OF THE INVENTION

I have found that a composition comprising a fertilizer composition, preferably in a slow release encapsulated form, a specific high commmpressive strength plaster, also called gypsum cement, and finely divided carbon particles can provide efficient release and fertilization of plants throughout the temperate season. The novel slow release fertilizer composition can be distributed in the environment in a variety of forms, spheres, cylinders, polygons, blocks, etc. For reasons of each of manufacture and controlled decomposition, it is most commonly distributed in the environment in the form of a cylinder or truncated cone (a tapered cylinder) which slowly dissolves in the presence of moisture during the temperate season until it is substantially gone. The fertilizer composition in combination with plaster or gypsum cement provides a continual smooth release at a constant rate resulting in the constant effective fertilizing concentration of fertilizer elements in the environment without releasing intermittanty excessive amounts of fertilizer elements. The plaster tends to dissolve at a near steady rate in the presence of environmental water, releasing fertilizer into the environment. The dissolution is most effective when the fertilizer means is fully below the surface of the cultivated farm area in contact with natural water which resides between soil particles. The soil water, by osmotic or capillary action, migrates into the fertilizer release means and begins to dissolve the plaster. As the plaster is removed by water action the fertilizer is revealed and is released depending on the rate the plaster is dissolved. The carbon acts as a secondary release mechanism. As the fertilizer is adsorbed and re-releases slowly from the carbon particle, a more constant rate of release of the fertilizer results. Further, carbon particles have a large surface area which can absorb the excess fertilizer as it is released, smoothing its release into the environment. Accordingly, each of the components of the composition cooperates with the other components, providing smooth, effective fertilizer release during the entire temperate season.

DETAILED DISCUSSION OF THE INVENTION

Briefly, the controlled slow release fertilizer composition comprises a fertilizer composition, a specific high strength plaster or gypsum cement composition, and finely divided carbon particles. The fertilizer means made of the controlled slow release fertilizer composition must have a specific surface area to provide an effective concentration of fertilizer.

FERTILIZER

The major emphasis of developing modern fertilizers is the determination of the most effective and economical means for supplying the nutrient elements. Most elements are supplied as compounds rather than in elementary form. Since compounds containing the elements are less expensive and more suitable for plant use, the major emphasis on the consumption of macro-nutrients in agriculture are directed to nitrogen, phosphorous and potassium nutrients, even though other nutrients are essential to plant growth.

Nitrogen is supplied either in the form of an ammonia compound or in a nitrate compound. In general agricultural practice, there is little difference between the ammonia or nitrate form. Nitrifying bacteria are common in most soils and transform ammonia or ammonium species to nitrates rapidly. Problems with commercially important nitrogen materials include caking, hygroscopicity, fire and detonation hazards, nitrogen loss after application, nonuniform release of nitrogen to the plant during the growing period.

Phosphates are commonly supplied to the plant in two major forms as a calcium phosphate or as an ammonium phosphate. Calcium phosphate has been in use for many years, is called "Super Phosphate", and was the first commercial fertilizer of importance. Ammonium phosphates are relatively new materials developed during the 50's and are low in cost and high in nutrient value.

The source of fertilizer potassium is most commonly potash, since potash compounds are available in natural deposits around the world, and is satisfactory for use as mined. Potash is relatively soluble and readily absorbed by plants without further treating. However, many other potassium materials such as potassium sulfate, potassium nitrate and others are available if needed.

Secondary nutrients such as calcium, magnesium, and sulfur can be important if the soil is substantially depleted of these nutrients. Micro-nutrients including boron, chlorine, copper, iron, manganese, molybdenum, and zinc are usually supplied as soluble salts, however less soluble forms such as chelated and glass forms of the micro-nutrient compounds have been used.

PLASTER

Dehydration of gypsum calcium sulfate dihydrate, ($CaSO_4.2H_2O$) in an open kettle by direct heating in the range of 390°–570° F. will result in beta-calcium sulfate hemihydrate, $CaSO_4.0.5H_2O$, commonly called plaster. Typically the plaster crystals are long, needle-like, irregular in shape and porous. The shape and porosity of the crystalline particles results in high water absorbency. The powder, when mixed with water, will require about 60 parts of water to about 100 parts of plaster to give a "workable" consistency. Plasters can contain a variety of additives which provide properties such as wettability, strength, hardening rate, particle size, and low viscosity slurries.

Preferred plaster compositions having a controlled rate of disintegration or deterioration in the environment comprise plasters, also called gypsum cement, with a certain high compressive strength. These plasters can slowly disintegrate over a time period of 120 to 180 days and can deliver the fertilizer into the environment during the decomposition period.

The most preferred plaster for making the improved slow release fertilizer compositions of this invention comprise a high density, high compressive strength plaster having a density of at least 1,600 grams per liter and compressive strength of at least 5,000 lbs. per square inch, preferably 9,000 lbs. per square inch, more preferably about 10,000–15,000 lbs. per square inch and greater, for reasons of its slow decomposition in the environment, resulting in the extended lifetime of the composition in the environment and a sufficient concentration of the fertilizer agent throughout the temperature season.

While we do not wish to be held to a theory of action of the fertilizer means of this application, we believe that the high density, high compressive strength of the plaster is a result of the crystal structure of the calcium sulfate hydrate that makes up the plaster. The crystal structure of high compressive strength plaster results in a controlled steady state rate of solubility which in turn controls the release of the pesticide. The crystals in the plaster appear to overlap and interact, resulting in a high density plaster having increased compressive strength and a controlled rate of solubility resulting from the crystal structure. These properties appear to be essential in providing the controlled solubility and controlled release of the fertilizer compositions.

CARBON

Finely divided carbon compositions useful in the invention for making the delayed fertilizer composition of the invention are carbon compositions having large surface area and small particle size, providing the release smoothing properties. As the fertilizer means comprising the slow release composition decomposes, the fertilizer released. The carbon in the composition tends to smooth the release rate by absorbing extra concentrations of fertilizer when the release rate is high and by releasing or desorbing the fertilizer when the release rate is low.

Accordingly, preferred particulate carbon useful in the invention has large surface area and small particle size found in carbon sources such as activated carbon, finely divided charcoal, etc. further details of sources of finely divided carbon is found in Kirk-Othmer Encyclopedia of Chemical Technology, Second Edition, Volume IV, pages 149-335.

In somewhat greater detail, the slow release fertilizer composition is formed from an effective amount of a fertilizer compound, sufficient plaster to result in a slow dissolution of plaster lasting commonly from 5 to 140 days, sufficient amount of charcoal to promote smooth release of the fertilizer, and sufficient water to be workable in manufacture and to cause the mixture to form a solid object which can be distributed throughout the environment.

The slow release fertilizer composition can take the form of a fertilizer means having essentially any regular or irregular three-dimensional shape including spheres, oblate spheres; polygons such as cubes, dodecahedrons, pyramids; cylinders, pyramids, cones, truncated cones; pillows, briquettes, etc. The release rate of the pest control agent from the means appears to be proportional to the means' surface area. The surface area should range from about 50 to about 3,500 mm$^2$, preferably about 150 to 2500 mm$^2$ and most preferably about 300 to 750 mm$_2$, depending on the concentration of the fertilizer in the means, for reasons of economy and ease of handling. The preferred form of the slow release composition is in the form of a cylinder having dimensions of about 3 to 40 millimeters in diameter, and 3 to 20 millimeters in depth.

The most preferred form of the slow release composition is in the form of a truncated cone. I have discovered that in methods for manufacturing the slow release fertilizer object that in most processes for molding the objects the most difficult step is unmolding the objects. I have found that the form which leaves the mold intact with minimum breakage has the form of a truncated cone wherein the minor radius is formed at the bottom of the mold and the major radius is formed at the top. I have found that for reasons of ease of molding and balanced release of the slow release compositions, the major diameter of the truncated cone should be about 6 to 30 millimeters, that the minor diameter of the truncated cone should be from about 4 to 25 millimeters, and that the cone should be from about 5 to 20 millimeters in depth. Commonly the cone should have about 150 mg. to 5 grams of material.

The most preferred embodiment of the fertilizer means comprises a truncated cone, having an effective amount of a commercially available fertilizer, a major diameter of about 8 to 12 millimeters, a minor diameter of about 6 to 10 millimeters, a height of about 10 to 20 millimeters, a mass of about 250 to 1000 mg. and a total surface area of about 300 to 1,000 mm$^2$.

The composition can also be formed into objects having a substantial irregular shape, however sufficient amount of the composition should be included in the object so that substantial growth promoting concentrations of the fertilizer composition is present in the environment through the substantial portion of the temperate growing season.

The slow release fertilizer composition can comprise from about 15 to 80%, preferably about 20 to 75% and most preferably about 35 to 55% plaster, depending on the length of the temperate season. The slow release composition can comprise 80 wt-% or less of a fertilizer either encapsulated or unencapsulated, preferably 70% or less, most preferably for reasons of efficient plant growth throughout the temperate season about 5 to 50 wt-% of the fertilizer. Alternatively the amount of fertilizer excluding encapsulating material will be less than about 50 wt-%, preferably about 1 to 45 wt-%, most preferably about 3 to 40 wt-%. The composition can comprise less than about 10 wt-%, preferably less than about 8 wt-%, most preferably about 4 to 6 wt-% of charcoal or activated carbon in order to control the release of the insecticide composition. Sufficient water is added to the mixture of dry components sufficient to hydrate the plaster to bind the components together so that the composition can be formed into objects which can be distributed in the environment. Commonly an amount of water in the range of 25 to 50 wt-% of the composition can be present in the wet mix before molding. The water can be derived from the fertilizer compound or can be added separately.

Depending on the growing season and plant variety, fertilizer release can be maintained over varying time frames, depending on the surface area and composition of the fertilizer means distributed in the environment. Effective fertilizer release can be maintained for as little as 5-20 days and for as long as 150 days. An object having from 150 to 800 mg. of material can provide fertilizer release for 5 to 50 days. A fertilizer means object having from about 0.5 to 5 grams can provide a controlling amount of fertilizer agent for 40 to 150 days.

In general, depending on the amount of fertilizer in the fertilizer means, we have found that the fertilizer means can be applied to an agricultural site at a rate that provides about 5 to 250 pounds of nitrogen, about 5 to 125 pounds of phosphorous (as $P_2O_5$), up to 150 pounds of potassium, up to about 1,000 pounds of calcium (depending on soil conditions), up to about 5,000 pounds of magnesium, and about 0.1 to 10 pounds of micro-nutrients per acre. The fertilizer means of this invention is commonly distributed throughout an agricultural area before planting and is cultivated into the earth at a depth where it can come in contact with sufficient water in the soil in order to begin the dissolution of the plaster matrix. Commonly the fertilizer means is not buried at a depth of greater than about 7 to 10 inches, since at greater depths fertilizer compounds would be substantially less available to growing plant root systems. Most commonly the fertilizer means is placed on the soil and cultivated so that it is at least 1 inch below the surface and about 7 inches or less in depth, insuring sufficient contact with water while the fertilizer means releases the fertilizer at a controlled rate at a soil location convenient to root systems.

The fertilizer means can be distributed into the environment by hand, can be distributed from ground vehicles or boats, can be distributed by helicopter or other aircraft, or any other means insuring a fairly even distribution in the environment. The fertilizer means of the invention can be distributed into any agricultural soil which contains sufficient water to slowly dissolve the plaster.

Typical agricultural locations suitable for introduction of the fertilizer means include fields for the production of corn, soybeans, wheat, rice, alfalfa, and other grains, fields for the production of produce such as tomatoes, cucumbers, lettuce, grapes, cabbage, peanuts, celery, etc., fruits such as oranges, grapefruit, lemons, apples, pears, berries, etc. Virtually any liquid or solid fertilizer can be either encapsulated or nonencapsulated, can be incorporated into the fertilizer means of the invention and can be distributed into the field.

EXAMPLE I

Into a 15 gallon steel tank is placed 40 pounds of a mixture of granulated ammoniated super phosphate and potassium chloride (18-46-2) and 4 gallons of water. The mixture was agitated until a smooth slurry formed with a mortar mix paddle attached to a hand held drill driven at 800 rpm. Into the uniform slurry is added 4 lbs. Norit SG charcoal powder and the mixture is again agitated until uniform. Into the mixture is placed 62 lbs. of plaster (DieKeen dental plaster, compressive strength 13,500 psi), 3.3 quarts of water and 500 grams of plaster set accelerator (Terra Alba). The mixture is agitated with the mortar mix paddle for eight minutes until fully mixed. The mixture is creamy within four minutes indicating that the plaster is fully wetted.

The slow release fertilizer mixture is poured onto an RTV rubber mold having 1100 individual molds each in the form of a cylinder having approximate dimensions of 12 millimeters in diameter and 5 millimeters in height. Each of the molds accepts about 600 to 650 mg. of plaster material. After the plaster mixture is added to the molds, the plaster mixture is distributed throughout the mold sheet with a spatula, the mold is tapped to release trapped air, and the excess plaster is removed from the top of the mold with the float which also evened the material. The plaster objects harden within about one and one half hours and are popped from the rubber mold into a trough, and are then ready for bagging The compressive strength of the objects ranged from 220-350 psi.

The introduction of the fertilizer means, at a rate bringing to the soil about 20 pounds of nitrogen, 12 pounds of phosphorous (as $P_2O_5$) and 10 pounds of potassium oxide per acre, slowly released the fertilizer throughout the first 70 days of the growing season, did not burn crop growth, did not harm root systems, and resulted in increased production.

The above discussion and Examples provides a basis for understanding and practicing the invention. However, since many embodiments of the invention can be made without departing from the spirit and scope of the invention, the invention resides solely in the claims hereinafter appended.

I claim:

1. A controlled slow release fertilizer composition that can be hardened by the addition of a sufficient plaster hydrating amount of water, which consists essentially of about 5 to 80 wt-% of a fertilizer composition, about 20 to 80 wt-% of a plaster having high compressive strength of at least about 5,000 lbs. per square inch, and about 4 to 10 wt-% of an effective fertilizer release smoothing finely divided carbon, wherein the composition can be used in the form of a solid fertilizer means in an agricultural site to release fertilizer by dissolution of the plaster.

2. The composition of claim 1 wherein the fertilizer composition comprises a source of nitrogen, a source of phosphorous, a source of potassium, or mixture thereof.

3. The composition of claim 1 wherein the fertilizer composition is an encapsulated fertilizer composition.

4. The composition of claim 3 wherein the encapsulated fertilizer composition is present in the total encapsulated composition at an amount of about 50 wt-% or less.

5. The composition of claim 4 wherein the fertilizer composition is ammoniated superphosphate.

6. The composition of claim 4 wherein the fertilizer composition is ammonium diphosphate.

7. The composition of claim 1 wherein the compressive strength of the high compressive strength plaster ranges from about 9,000 to about 15,000 pounds per square inch.

8. The composition of claim 7 wherein the compressive strength of the high compressive strength plaster ranges from about 10,000 to 14,000 pounds per square inch.

9. The composition of claim 1 wherein the fertilizer composition is present in the total composition in an amount of about 3 to about 16 wt-%.

10. The composition of claim 1 wherein the plaster is present in the total composition in an amount of about 30 to 90 wt-%.

11. The composition of claim 1 wherein the finely divided carbon is present in the total composition in an amount of about 1 to about 15 wt-%.

12. A controlled slow release solid fertilizer means which comprises a uniform solid that consists essentially of about 5 to 80 wt-% of a fertilizer composition, about 15 to 80 wt-% of a high compressive strength plaster, about 4 to 10 wt-% of finely divided carbon particles, and a plaster hardening amount of water, wherein the cast solid has a surface area of about 500 to about 50,000 mm$^2$, and wherein the fertilizer means can be introduced into an agricultural site to release fertilizer by dissolution of the plaster.

13. The solid fertilizer means of claim 12 wherein the surface area of the cast solid is about 150 to 2,500 mm$^2$.

14. The solid fertilizer means of claim 13 wherein the surface area of the cast solid is about 300 to 750 mm$^2$.

15. The solid fertilizer means of claim 12 wherein the means has a regular shape.

16. The solid fertilizer means of claim 15 wherein the regular shape is a briquette, a pillow, a sphere, a prism, or a pyramid.

17. The solid fertilizer means of claim 15 wherein the regular shape is a cylinder having dimensions of about 3 to 40 millimeters in diameter and about 3 to 40 millimeters in height.

18. The fertilizer means of claim 17 wherein the dimensions of the truncated cone are about 8 to 12 millimeters in the major diameter, about 6 to 10 millimeters in the minor diameter, and about 10 to 20 millimeters in height.

19. The fertilizer means of claim 18 wherein the surface area of the fertilizer means is about 300 to 1,000 mm$^2$ and wherein the mass of the fertilizer means is about 250 to 1,000 milligrams.

20. The fertilizer means of claim 15 wherein the regular shape is a truncated cone having dimensions of about 6 to 30 millimeters on the major diameter, about 4 to 25 millimeters on the minor diameter, and about 5 to 20 millimeters in height.

21. A method of fertilizing agricultural land which comprises distributing the solid fertilizer means of claim 12 into an agricultural environment.

22. The method of claim 21 wherein the solid fertilizer means are applied uniformly in the agricultural environment at a rate providing about 5 to 50 pounds of nitrogen, about 5 to 125 pounds of phosphorous or up to 150 pounds of potassium per acre.

23. The method of claim 22 wherein the solid fertilizer means is applied uniformly at a depth of less than about 7 inches but greater than about 1 inch.

* * * * *

UNITED STATES PATENT AND TRADEMARK OFFICE
CERTIFICATE OF CORRECTION

PATENT NO. : 4,670,039
DATED : June 2, 1987
INVENTOR(S) : ROBERT D. SJOGREN

It is certified that error appears in the above-identified patent and that said Letters Patent is hereby corrected as shown below:

Column 1, line 42, for "magmesium" read --magnesium--.
Column 2, line 14, for "commpressive" read --compressive--.
Column 2, line 30, for "intermittantly" read --intermittently--.
Column 4, line 25, for "fertilizer released" read --fertilizer is released--.
Column 4, line 56, for "$mm_2$" read --$mm^2$--.
Column 5, line 40, for "insecticide" read --fertilizer--.
Column 7, line 25, for "mixture" read --mixtures--.

Signed and Sealed this

First Day of December, 1987

Attest:

DONALD J. QUIGG

Attesting Officer

Commissioner of Patents and Trademarks